United States Patent [19]

Bettarini et al.

[11] Patent Number: 5,418,246
[45] Date of Patent: May 23, 1995

[54] OXA(THIA)DIAZOL- AND TRIAZOL-ONES(THIONES) HAVING A MITICIDE AND INSECTICIDE ACTIVITY

[75] Inventors: Franco Bettarini; Luigi Capuzzi; Piero La Porta, all of Novara; Sergio Massimini, Milan; Vincenzo Caprioli, San Martino Siccomario, all of Italy

[73] Assignee: Ministero Dell 'Universita' E Della Ricerca Scientifica E Technologica, Rome, Italy

[21] Appl. No.: 945,135

[22] Filed: Sep. 15, 1992

[30] Foreign Application Priority Data

Sep. 17, 1991 [IT] Italy .................. MI91A2456

[51] Int. Cl.⁶ .................. C07D 271/113; A01N 43/824
[52] U.S. Cl. .................. 514/364; 548/144; 548/136; 548/203.2
[58] Field of Search .................. 548/144; 514/364

[56] References Cited

U.S. PATENT DOCUMENTS 4,943,583  7/1990  Lüthy .................. 514/364
5,093,343  3/1992  Bayer .................. 514/363

OTHER PUBLICATIONS

Goswam I, J. Het Chem. 21, 205 (1984).
Goswami II Indian J. Chem. Sect B 23B 796 (1984).
Chemical Abstracts No. 211056, vol. 101, 1984 Columbus, Ohio.
Chemical Abstracts No. 143266, vol. 114, 1991 Columbus, Ohio.
Chemical Abstracts No. 231403, vol. 113, 1990 Columbus, Ohio.

Primary Examiner—Robert Gerstl
Attorney, Agent, or Firm—Rogers & Wells

[57] ABSTRACT

A description follows of oxa(thia)diazol- and triazol-ones(thiones), with a miticide and insecticide activity, having the general formula

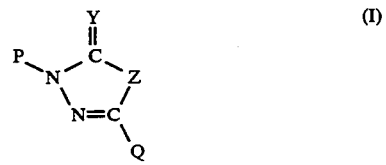

(I)

wherein:
Y=O, S; Z=O, S, NCH₃, one of the two substituents P and Q is an ortho-substituted phenyl and the other a substituted benzyl.

10 Claims, No Drawings

OXA(THIA)DIAZOL- AND TRIAZOL-ONES(THIONES) HAVING A MITICIDE AND INSECTICIDE ACTIVITY

The present invention relates to new heterocyclic compounds having a miticide and insecticide activity, the procedures for their preparation, the miticide and insecticide compositions containing these compounds and the use of said compositions for controlling mites and insects which are harmful in agricultural, civil and zootechnical fields. More specifically, the invention relates to oxy(thia)diazol- and triazol-ones(thiones) including: 1,3,4,-oxadiazol-2-(3H)-ones, 1,3,4-oxadiazol-2(3H)-thiones, 1,3,4-thiadiazol-2(3H)-ones, 1,3,4-thiadiazol-2(3H)-thiones, 2,4-dihydro-3H-1,2,4-triazol-3-ones and 2,4-dihydro-3H-1,2,4-triazol-3-thiones; having strong miticide and insecticide activities.

European Patent 270061 discloses heterocyclic compounds with miticide and insecticide activity having the general formula A

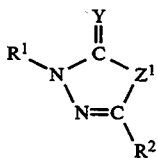

(A)

wherein among the various meanings:
Y=O, S; $Z^1$=O, S, $NCH_3$:
$R^1$=phenyl or pyridyl optionally substituted.
$R^2$=phenyl having at least one orthosubstituted position.

It has now been unexpectedly found that by modifying the compounds of formula A in such a way that one of the two substituents $R^1$ and $R^2$ is a substituted benzyl and the other an orthosubstituted phenyl, miticide and insecticide compounds are obtained having a greater activity particularly on the eggs and young forms of mites.

The present invention consequently relates to oxa(thia) diazol- and triazol-ones(thiones) having the general formula:

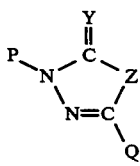

(I)

wherein:
Y represents O, S
Z represents O, S or an NMe group wherein Me=-methyl;
P represents an Fp group or a Bp group;
Q represents a Bq group when P=Fp, or an Fq group when P=Bp and Z=O or S;

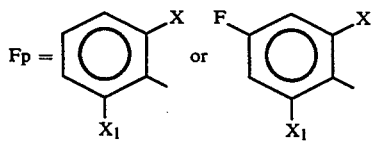

-continued

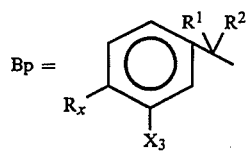

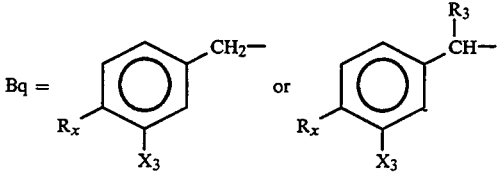

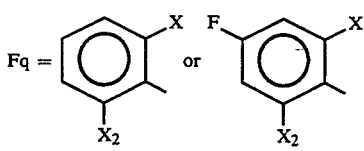

in said Fp, Fq, Bp and Bq groups:
X represents Cl, F, Br, Me, MeO;
$X_1$ represents H or F;
$X_2$ represents H, F, or Cl;
$X_3$ represents H, F, Cl or a $C_1$–$C_4$ alkoxy;
$R_1$ and $R_2$ independently represent H or a $C_1$–$C_3$ alkyl;
$R_x$ represents a $C_3$–$C_{10}$ alkoxy, a $C_3$–$C_8$ alkenyloxy a $C_3$–$C_8$ alkinyloxy, a $C_3$–$C_8$ cycloalkoxy, a $C_4$–$C_8$ cycloalkylalkoxy, a $C_3$–$C_{10}$ alkoxyalkoxy all optionally halogenated, or a phenoxy or a phenylalkoxy optionally substituted by halogen atoms, alkyl groups, halo-alkyl groups, alkoxy groups, halo-alkoxy groups; $R_3$ represents a $C_1$–$C_3$ alkyl.

The compounds of the present invention can be prepared according to various procedures, outlined below, depending on the meaning of the symbols P, Q, Y and Z in general formula I.

In the following formulae (reaction schemes 1–6), the symbols Z, Y, P, Q, Fp, Fq, Bp, Bq, X, $X_1$, $X_2$, $X_3$, $R_1$, $R_2$, $R_x$ have the meanings specified above.

In general, compounds having formula I can be prepared by the sequence of reaction shown in scheme 1: a hydrazide or thiohydrazide having general formula II (where $Z_1$ represents O or S) is reacted with a suitable cyclization agent (AC) to give the compounds having general formula I wherein Z represents 0 or S (Ia, where $Z_1$ represents O or S) [reaction 1A]; the compounds having general formula I wherein Y represents O and Z represents NMe (Ic), can be prepared from the corresponding compounds having general formula I wherein Y and Z represent O, P represents an Fp group and Q represents a Bq group (Ib), obtained by reaction 1A, by treatment with methylamine and closing of the acyl semicabazide intermediate having general formula IV by heating in a basic environment [reaction 1B]; the compounds having general formula I wherein Y represents S (Ie) can be prepared from the corresponding compounds having general formula I wherein Y represents O (Id), obtained by means of reactions 1A and 1B, by treatment with a sulphonating agent (AS) [reaction 1C]: scheme 1 scheme 1

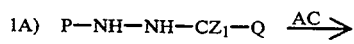

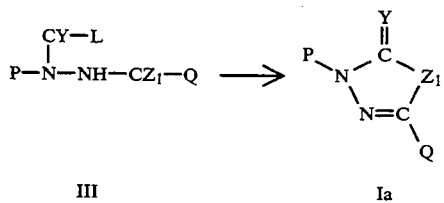

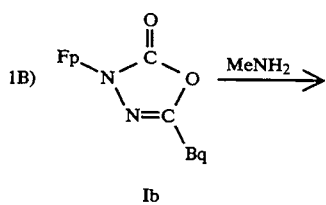

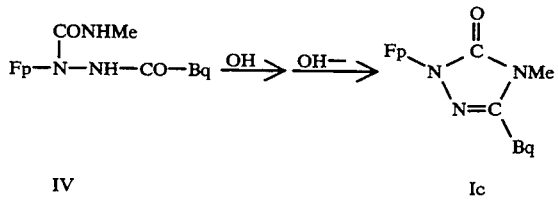

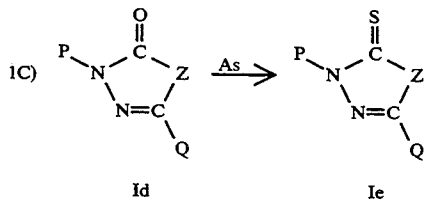

The cyclization reaction 1A can be carried out in a single step, or in two steps; in the latter case an intermediate having general formula III is first isolated and is converted into the product having general formula Ia with subsequent treatment. The following may be used as cyclization agents (AC): phosgene, trichloromethyl chloroformiate (diphosgene), an alkyl (for example methyl or ethyl) benzyl or phenylchloroformiate, when Y=O; thiophosgene or carbon sulphide when Y=S.

In general formula III, L represents Cl; or $R_LO$ (with $R_L$=CCl$_3$, alkyl, benzyl or phenyl) provided that Y represents O; or S provided that Y represents S.

When phosgene, trichloromethyl chloroformiate or thiophosgene are used, the preparation of the compounds having general formula Ia is suitably carried out in a single step, by treating the (thio)hydrazide having formula II, dissolved or suspended in a suitable solvent, with the cyclization agent (possibly also dissolved in the reaction solvent), at a temperature ranging from 20° C. to the boiling point of the reaction mixture and possibly in the presence of a base. Solvents which can be used for the reaction are, for example, methylene chloride, chloroform, 1,2-dichloroethane, benzene, toluene, xylene, chlorobenzene, ethyl ether, tetrahydrofuran, dioxane, ethyl acetate. Bases which can be used are sodium bicarbonate, triethylamine, pyridine, 4-dimethylaminopyridine.

When an alkyl, benzyl or phenyl chloroformiate are used, the reaction is generally carried out in two steps. The hydrazide having general formula II, dissolved or suspended in an inert solvent (selected for example from those listed above), is treated with the ester of chloroformic acid in the presence of a base (for example triethylamine), at a temperature ranging from 0° C. to the boiling point of the reaction mixture; the intermediate having general formula III (L=alkoxy, benzyloxy or phenoxy) obtained from the reaction, is subsequently cyclized by heating to a temperature of 120° to 200° C., possibly in the presence of a high-boiling solvent (for example xylene or ortho-dichlorobenzene) and a base (for example dimethyl-aminopyridine), as described in the Journal Heterocyclic Chemistry 23 (1986), pages 417–419.

When carbon sulphide is used as cyclization agent, the reaction is generally carried out in a protic solvent (for example ethanol, methylcellosolve, water) in the presence of strong bases such as sodium carbonate, potassium carbonate, sodium methylate etc., at temperatures ranging from 0° C. to the reflux temperature of the reaction mixture; the intermediate having formula III (where Y=S, L=S) is cyclized by treatment with mineral acids, for example hydrochloric acid.

Conversion 1B can be suitably carried out [as described in European Patent Application 301946] by adding methylamine (in a gaseous form or aqueous solution) to the oxadiazolone having formula Ib dissolved in an inert solvent, reflux heating until the starting product has disappeared, cooling to room temperature, adding an aqueous solution or sodium or potassium carbonate and again heating the reaction mixture to reflux temperature. Solvents which can be used for the reaction are, for example, tetrahydrofuran, dioxane, dimethoxyethane, diethoxyethane etc. Reaction 1C is carried out by adding the sulphurating agent to the compound having formula Id dispersed in an inert organic solution, such as dimethoxyethane, dioxane, toluene, xylene, chlorobenzene, ortho-dichlorobenzene, and heating the mixture to a temperature ranging from 80° C. to the boiling point of the reaction mixture; sulphurating agents which can be used are phosphorous pentasulphide, 2,4-bis-(methoxyphenyl) -1,2,dithioxo-1,3,2,4-dithiadiphosphethane (Lawesson reagent),2,4-bis(p-tolylthio)-1,3,2,4-dithiadiphosphethane-2,4-disulphide, 2,4-bis(methylthio)-1,3,2,4-dithiadiphosphethane-2,4-disulphide.

The compounds having general formula Ic can alternatively be prepared [as described in Annalen der Chemie 675 (1964), pages 180–188] by the reaction of a hydrazide having general formula IIa with methyl isocyanate, and cyclization in a basic environment of acyl semicarbazide having formula IV (reaction scheme 2):

Scheme 2

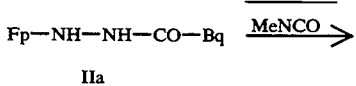

-continued
Scheme 2

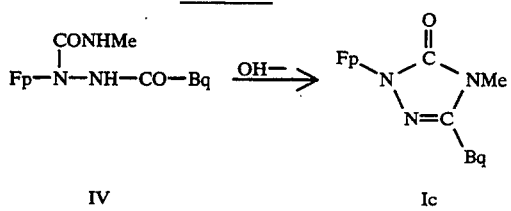

The acyl semicarbazide having formula IV is prepared by adding methyl isocyanate to the hydrazide IIa dispersed in an inert organic solvent (for example methylene chloride, chloroform, 1,2-dichloroethane, benzene, toluene, xylene, chlorobenzene, ethyl ether, tetrahydrofuran, dioxane, ethyl acetate, etc), and keeping the reaction mixture at a temperature ranging from 0° C. to the reflux temperature; the cyclization of the acyl semicarbazide is carried out, as described above, by adding an aqueous solution of sodium or potassium carbonate to a solution having formula IV in an inert solvent (for example tetrahydrofuran, dioxane, dimethoxyethane, diethoxyethane, etc) and heating up to reflux temperature.

The compounds having general formula I wherein P represents Bp, Q represents Fq, Z and Y represent O (general formula If), can alternatively be prepared, with a similar procedure to that described in the Journal Heterocyclic Chemistry 21 (1984), pages 397–400, by the reaction of an acylhydrazone having general formula V with an alkyl chloroformiate (for example ethyl chloroformiate), and subsequent treatment of O-alkoxycarbonyl-hydrazone having formula VI, where R=C$_1$-C$_4$ alkyl, with sodium boro hydride (reaction scheme 3):

Scheme 3

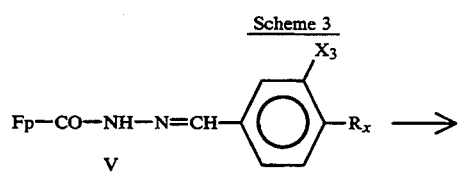

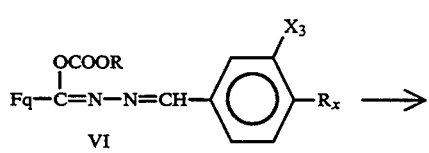

The reaction of acyl hydrazone V with alkyl chloroformiate is carried out in an inert organic solvent, such as chloroform, 1,2-dichloroethane, benzene, toluene, tetrahydrofuran, dioxane, in the presence of a base (for example triethylamine) at a temperature ranging from 0° C. to the boiling point of the reaction mixture.

The reaction of O-alkoxycarbonyl-hydrazone having formula VI with sodium boro hydride is carried out in an inert solvent (for example tetrahydrofuran, dioxane, dimethoxyethane, diethoxyethane), preferably at the boiling point of the reaction mixture.

The starting products of general formulae II and V can be prepared according to various methods described in chemical literature.

The hydrazides having general formula II wherein P=Fp, Q=Bq and Z$_1$=O (IIa), can be obtained according to what is described in "Methoden der Organischen Chemie" (Houben Weil), 1985 Vol E5, pages 1154–1170; for example, by reacting a phenylhydrazine having formula VII with the chloride of a substituted phenylacetic acid having formula VIII (reaction scheme 4):

Scheme 4

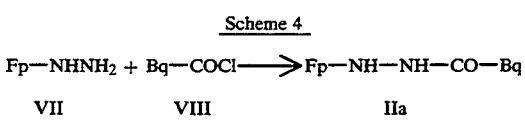

The hydrazides having general formula II wherein P=Bp, Q=Fq and Z$_1$=O (IIb), can be prepared (reaction scheme 5) by the condensation of a benzaldehyde having formula IX with a hydrazide having formula X to give the hydrazones having formula V; these, which can be alternatively used as starting products in reaction scheme 3, are then reduced to hydrazides IIb, as described, for example, in the Journal Chemical Society, (1929) pages 1941–1945, and in the Journal American Chemical Society, 79 (1957), pages 14–417:

Scheme 5

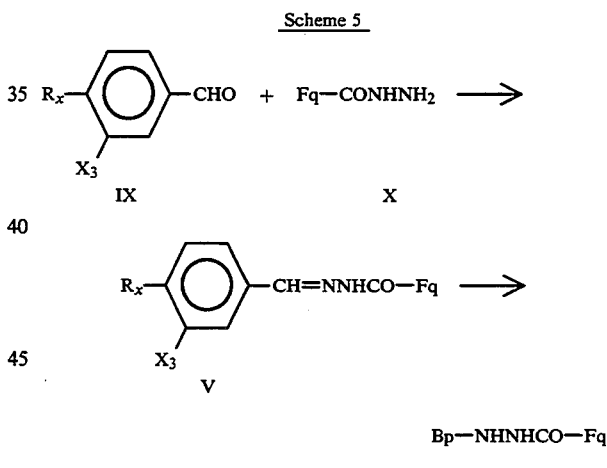

The compounds having general formula II wherein Z$_1$ represents S (IId) can be prepared from the corresponding oxygenated compounds IIc, for example by treatment with a sulphuring agent (phosphorous pentasulphide, Lawesson reagent etc.) as described in the Journal Heterocyclic Chemistry 23 (1986), pages 417–419 (reaction scheme 6):

Scheme 6

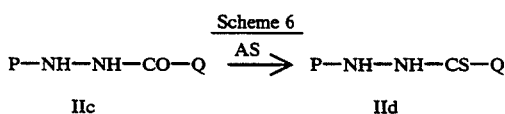

As already mentioned, the compounds having general formula I have a high miticide and insecticide activity, which is particulary effective against the eggs and young forms of important species of Tetranichides, Tarsonemides, Eriophydes, Ixodides, Argassides, Homocters, Heterocters. At the same time, the compounds of the present invention have a low toxicity with respect to many useful insects, mammals, fish, amphibia, birds, and they are not phytotoxic.

Thanks to their positive characteristics, they can consequently be advantageously used to protect agricultural and horticultural cultivations, domestic animals and livestock, manfrequented environments from mites and harmful insects.

For their practical use in both agriculture and other fields, it is advisable to use the compounds of the invention in the form of-suitable compositions.

These compositions can contain, apart from one or more of the compounds having formula I as the active principle: solid inert carriers (such as kaolin, alumina, silica, talc, bentonite, chalk, quartz, dolomite, attapulgite, montmorillonite, diatomee earth, cellulose, starch, etc.); liquid inert carriers (organic solvents such as aromatic or aliphatic hydrocarbons possibly chlorinated, alcohols, esters, ketones, etc. vegetable or mineral oils, water and their mixtures); surface-active agents (wetting and emulsifying agents of the non-ionic, anionic, cationic type); dispersing agents (lignin and its salts, derivatives of cellulose, alginates, etc.); stabilizers (antioxidants, UV absorbents, etc.).

To widen the field of action of the compositions it is possible to add other active ingredients such as, for example, other insecticides or miticides, weed-killers, fungicides, fertilizers.

It can be particularly advantageous to combine the compounds of the invention with other miticides which act on mobile forms of mites, such as for example propargite, dicofol, chlorobenzylate, benzoxymate, bromopropylate, fenbutatin oxide, methidathion, cyhexatin, amitraz, avermectin, fluvalinate, bifenthrin, acrinathrin, etc.

The dosages to be applied depend on various factors such as the type and degree of infestation, the type of composition used, climatic and environmental factors.

For practical use in agriculture, dosages of the compound of 25 g to 500 g per hectare give sufficient protection.

The following examples provide a better illustration of the invention.

EXAMPLE 1

3-(2-Chlorophenyl)-5-(4-n-propoxybenzyl)-1,3,4-oxadiazol-2(3H)-one (compound 1)

4.95 g (25 mmoles) of trichloromethyl chloroformiate are charged into a 250 ml three-necked flask; 6.15 g (19.3 mmoles) of 2-chloro-N'-(4-n-propoxybenzyl)-benzhydrazide, dissolved in 90 ml of toluene are added dropwise at room temperature. The reaction mixture is heated to 100° C. for 4 h, under stirring and in a nitrogen atmosphere, and then concentrated at reduced pressure to eliminate the solvent and excess reagent. The residue is diluted with ethyl ether and washed with water until neutral; the ether phase is anhydrified with sodium sulphate and concentrated at reduce pressure. The reaction crude product is purified with silica gel chromatography, using hexane/ethyl acetate 85:15 as eluant. 3.8 g of pure product are obtained: m.p. 68 ° C. $^1$H-NMR (CDCl$_3$): δ at 1.0 (t, 3H); 1.5–2.0 (m, 2H); 3.7 (s, 2H); 3.75 (t, 2H); 6.7–7.6 (complex, 8H).

EXAMPLE 2

3-(2-Chlorophenyl)-5-(4-iso-propoxybenzyl)-1,3,4-oxadiazol-2(3H)-one (compound 2 )

The product is obtained following the procedure described in Example 1, starting from 2-chloro-N'-(4-iso-propoxybenzyl)benzhydrazide and trichloromethyl chloroformiate: m.p. 54° C.

$^1$H-NMR (CDCl$_3$): 1.3 (d, 6H); 3.85 (s, 2H); 4.5 (m, 1H); 6.7–7.5 (complex, 8H).

EXAMPLE 3

5-(4-n-Butoxybenzyl)-3-(2-chlorophenyl)-1,3,4-oxadiazol-2(3H)-one (compound 3 )

The product is obtained following the procedure described in Example 1, starting from N'-(4-n-butoxybenzyl)-2-chlorobenzhydrazide and trichloromethyl chloroformiate: m.p. 63° C.

1H-NMR (CDCl$_3$): 0.9 (t, 3H); 1.1–1.85 (m, 4H); 3.8 (s, 2H); 3.85 (t, $^2$H); 6.6–7.7 (complex, 8H).

EXAMPLE 4

5-(4-sec-Butoxybenzyl)-3-(2-chlorophenyl)-1,3,4-oxadiazol-2(3H)-one (compound 4 )

The product is obtained following the procedure described in Example 1, starting from N'-(4-sec-butoxybenzyl)-2- chlorobenzhydrazide and trichloromethyl chloroformiate.

1H-NMR (CDCl$_3$): 0.95 (t, 3H); 1.3 (d, 3H); 1.4–1.85 (m, 2H); 3.8 (s, $^2$H); 4.25 (m, 1H); 6.5–7.6 (complex, 8H).

EXAMPLE 5

3-(2-chlorophenyl)-5-[4-(1-ethylpropoxy)benzyl]-1,3,4-oxadiazol-2(3H)-one (compound 5)

The product is obtained following the procedure described in Example 1, starting from 2-chloro-N'-[4-(1-ethylpropoxy)benzyl]-benzhydrazide and trichloromethyl chloroformiate.

$^1$H-NMR (CDCl$_3$): 0.9 (t, 6H); 1.1–1.9 (m, 4H); 3.75 (s, 2H); 4.0 (m, 1H); 6.6–7.5 (complex, 8H) .

EXAMPLE 6

3-(2-chlorophenyl)-5-[4-phenoxybenzyl]-1,3,4-oxadiazol-2(3H)-one (compound 6)

The product is obtained following the same procedure described in Example 1, starting from 2-chloro-N'-[4-phenoxybenzyl]-benzhydrazide and trichloromethyl chloroformiate: m.p. 85° C.

$^1$H-NMR (CDCl$_3$: δ at 3.8 (s, 2H); 6.7–7.5 (complex, 13H).

EXAMPLE 7

Following the procedure described in Example 1, the following oxadiazolones were prepared starting from the corresponding benzhydrazide and trichloromethyl chloroformiate: 5-(4-sec-Butoxybenzyl)-3-(2,6-difluorophenyl)-1,3,4-oxadiazol-(2(3H)-one (compound 7). $^1$H-NMR (CDCl$_3$): 0.9 (t, 3H); 1.25 (d, 3H); 1.35–1.80 (m, 2H); 3.80 (s, 2H); 4.2 (m, 1H); 6.7–7.5 (complex, 7H).

5-(4-iso-Butoxybenzyl)-3-(2-chlorophenyl)-1,3,4-oxadiazol-2(3H)-one (compound 14). $^1$H-NMR (CDCl$_3$): 1.0 (d, 6H); 2.0 (m, 1H); 3.7 (d, 2H); 3.8 (s, 2H); 6.7–7.6 (complex, 8H).

5-(4-sec-Butoxybenzyl)-3-(2-methylphenyl)-1,3,4-oxadiazol-2(3H)-one (compound 15). $^1$H-NMR (CDCl$_3$): 1.0 (t, 3H); 1.3 (d, 3H); 1.5–1.9 (m, 2H); 2.3

(s, 3H) 3.9 (s, 2H); 4.3 (m, 1H); 6.8–7.45 (complex, 8H).

5-(4-Cyclopentoxybenzyl)-3-(2-chlorophenyl)-1,3,4-oxadiazol-2(3H)-one (compound 16). $^1$H-NMR (CDCl$_3$): 1.45–2.05 (complex, 8H); 3.85 (s, 2H); 4.75 (m, 1H); 6.75–7.6 (complex, 8H).

3-(2-Bromophenyl)-5-(4-sec-butoxybenzyl)-1,3,4-oxadiazol-2(3H)-one (compound 17). $^1$H-NMR (CDCl$_3$): 1.0 (t, 3H); 1.3 (d, 3H); 1.5–1.9 (m, 2H); 3.9 (s, 2H); 4.3 (m, 1H); 6.8–7.9 (complex, 8H).

3-(2-Chloro-4-fluorophenyl)-5-(4-iso-propoxybenzyl)-1,3,4-oxadiazol-2(3H)-one (compound 18). $^1$H-NMR (CDCl$_3$): 1.3 (d, 6H); 3.85 (s, 2H); 4.55 (m, 1H); 6.8–7.5 (complex, 7H).

5-[4-(3-Butin-2-oxy)benzyl]-3-(2-chlorophenyl)-1,3,4-oxadiazol-2(3H)-one (compound 19). $^1$H-NMR (CDCl$_3$): 1.65 (d, 3H); 2.5 (d, 1H); 3.9 (s, 2H); 4.85 (dq, 1H); 6.9–7.6 (complex, 8H).

3-(2-Chlorophenyl)-5-[1-(4-iso-propoxyphenyl)ethyl]-1,3,4-oxadiazol-2(3H)-one (compound 20). $^1$H-NMR (CDCl$_3$): 1.3 (d, 6H); 1.65 (d, 3H); 4.05 (q, 1H); 4.55 (m, 1H); 6.8–7.6 (complex, 8H).

3-(2-Chlorophenyl)-5-[4-(2-ethylbutoxy)benzyl]-1,3,4-oxadiazol-2(3H)-one (compound 21). $^1$H-NMR (CDCl$_3$): 0.95 (t, 6H); 1.3–1.6 (m, 4H); 1.55–1.75 (m, 1H); 3.85 (d, 2H); 3.9 (s, 2H); 6.8–7.6 (complex, 8H).

EXAMPLE 8

5-(2-chlorophenyl)-3-(4-iso-propoxybenzyl)-1,3,4-oxadiazol-2(3H)-one (compound 8)

2 g (6.32 mmoles) of 1-(2-chlorobenzoyl)-2-(4-iso-propoxybenzylidene)-hydrazine, 40 ml of anhydrous chloroform and 20 ml of triethylamine (143.5 mmoles) are charged into a 250 ml 3-necked flask, in a nitrogen atmosphere; the mixture is brought to reflux temperature, and a solution of 8.6 g (79 mmoles) of ethyl chloroformiate in 20 ml of anhydrous chloroform is added dropwise under stirring.

The reaction mixture is kept at reflux temperature for 2 h; after cooling, it is diluted with chloroform, washed with water and then with 1% hydrochloric acid. The organic phase is anhydrified with sodium sulphate and concentrated at reduced pressure. The residue obtained (2.6 g) is dissolved in 150 ml of dioxane; 0.84 g (22.2 mmoles) of sodium boro hydride are added in portions and the mixture is heated to reflux temperature for 4 h. It is cooled with an ice bath and diluted acetic acid is slowly added dropwise until the pH is clearly acid. The reaction mixture is concentrated at reduced pressure, recovered with water, extracted with ethyl acetate, anhydrified with sodium sulphate. After removing the solvent at reduced pressure, the product is purified by silica gel chromatography using hexane/ethyl acetate 9:1 as eluant: m.p. 53° C. $^1$H-NMR (CDCl$_3$): 1.25 (d, 6H); 4.5 (m, 1H); 4.85 (s, 2H); 6.7–7.8 (complex, 8H).

The following compounds were prepared using the same procedure:

3-(4-sec-Butoxybenzyl)-5-(2-chlorophenyl)-1,3,4-oxadiazol-2(3H)-one (compound 22). $^1$H-NMR (CDCl$_3$): 1.0 (t, 3H); 1.3 (d, 3H); 1.5–1.9 (m, 2H); 4.3 (m, 1H); 4.85 (s, 2H); 6.7–7.8 (complex, 8H).

3-(4-sc-Butoxybenzyl)-5-(2.6-difluorophenyl)-1,3,4-oxadiazol-2(3H)-one (compound 23). $^1$H-NMR (CDCl$_3$): 1.0 (t, 3H); 1.3 (d, 3H); 1.5–1.9 (m, 2H); 4.3 (m, 1H) 4.85 ( s, 2H); 6.7–7.5 (complex, 7H).

3-(4-sec-Butoxybenzyl)-5-(2.6-dichlorophenyl)-1,3,4-oxadiazol-2(3H)-one (compound 24). $^1$H-NMR (CDCl$_3$): 1.0 (t, 3H); 1.3 (d, 3H); 1.5–1.9 (m, 2H); 4.3 (m, 1H); 4.85 ( s, 2H); 6.8–7.5 (complex, 7H).

EXAMPLE 9

5-(4-n-Butoxybenzyl)-3-(2-chlorophenyl)-1,3,4-oxadiazol-2(3H)-thione (compound 9 )

1.5 g (4.5 mmoles ) of N'-(4-n-butoxybenzyl)-2-chlorobenzhydrazide and 25 ml of toluene are charged into a 100 ml 3-necked flask; 780 g (6.78 mmoles) of thiophosgene dissolved in 5 ml of toluene are added dropwise and the mixture is heated to reflux temperature, under stirring and, in a nitrogen atmosphere, for 4 h. The mixture is left to cool to 50° C. and 1.9 ml (13.65 mmoles) of triethylamine are added dropwise; stirring is continued for 2 h. After cooling the mixture is concentrated at reduced pressure, recovered with water, extracted with ethyl ether; the organic phase is washed until neutral, anhydrified with sodium sulphate and concentrated at reduced pressure. The product is purified by silica gel chromatography, using hexane/ethyl acetate 85:15 as eluant: m.p. 69° C.

$^1$H-NMR (CDCl$_3$): 0.9 (t, 3H); 1.2–1.8 (m, 4H); 3.85 (t, 2H); 3.9 (s, 2H); 6.6–7.6 (complex, 8H).

EXAMPLE 10

5-(4-sec-Butoxybenzyl)-3-(2-Chlorophenyl)-1,3,4-oxadiazol-2(3H)-thione (compound 10)

1.2 g (3.3 mmoles) of 5-(4-sec-butoxybenzyl)-3-(2-chlorophenyl)-1,3,4-oxadiazol-2(3H)-one (compound 4), 10 ml of toluene and 2 g (4.95 mmoles) of 2,4-bis-(4-methoxyphenyl)-1,2-dithioxo-1,3,2,4-dithiadiphosphethane (Lawesson reagent) are charged into a 50 ml flask; the mixture is stirred at reflux temperature for 15 h. A saturated aqueous solution of sodium chloride is added and extracted with ethyl ether; the organic phase is anhydrified with sodium sulphate and concentrated at reduced pressure. The product is purified by silica gel chromatography using hexane/ethyl acetate 8:2 as eluant.

$^1$H-NMR (CDCl$_3$): 0.95 (t, 3H); 1.25 (d, 3H); 1.35–1.8 (m, 2H); 3.9 (s, 2H); 4.2 (m, 1H); 6.5–7.6 (complex, 8H).

EXAMPLE 11

5-(4-sec-Butoxybenzyl)-3-(2,6-difluorophenyl)-1,3,4-oxadiazol-2(3H)-thione (compound 11)

The product is prepared following the procedure described in Example 9, starting from N'-(4-sec-butoxybenzyl)-2,6-difluorobenzhydrazide and thiophosgene.

$^1$H-NMR (CDCl$_3$): 0.95 (t, 3H); 1.3 (d, 3H); 1.4–1.8 (m, 2H); 3.9 (s, 2H); 4.2 (m, 1H); 6.65–7.5 (compound, 7H) .

EXAMPLE 12

Following the procedure described in Example 1, the following thiadiazolones were prepared starting from the corresponding benzothiohydrazide and trichloromethyl chloroformiate:

5-(4-sec-Butoxybenzyl)-3-(2,6-difluorophenyl)-1,3,4-thiadiazol-2(3H)-one (compound 12). $^1$H-NMR (CDCl$_3$): 0.9 (t, 3H); 1.25 (d, 3H); 1.35–1.80 (m, 2H); 3.80 (s, 2H); 4.2 (m, 1H); 6.6–7.4 (complex, 7H).

5-(4-sec-Butoxybenzyl)-3-(2-chlorophenyl)-1,3,4-thiadiazol-2(3H)-one (compound 25). $^1$H-NMR (CDCl$_3$): 1.0 (t, 3H); 1.3 (d, 3H); 1.5–1.9 (m, 2H); 4.0 (s, 2H); 4.3 (m, 1H); 6.8–7.6 (complex, 8H).

5-(4-iso-Butoxybenzyl)-3-(2-chlorophenyl)-1,3,4-thiadiazol-2(3H)-one (compound 26). $^1$H-NMR (CDCl$_3$): 1.05 (d, 6H); 2.1 (m, 1H); 3.75 (d, 2H); 4.0 (s, 2H); 6.8-7.6 (complex, 8H).

3-(2-Chorophenyl)-5-(4-iso-propoxybenzyl)-1,3,4-thiadiazol-2(3H)-one (compound 27). $^1$H-NMR (CDCl$_3$): 1.35 (d, 6H); 4.0 (s, 2H); 4.55 (m, 1H); 6.8-7.6 (complex, 8H).

5-(4-sec-Butoxybenzyl)-3-(2-methoxyphenyl)-1,3,4-thiadiazol-2(3H)-one (compound 28). $^1$H-NMR (CDCl$_3$): 0.95 (t, 3H); 1.3 (d, 3H); 1.5-1.85 (m, 2H); 3.85 (s, 3H); 3.95 (s, 2H); 4.3 (m, 1H); 6.75-7.5 (complex, 8H).

5-(4-Sec-Butoxybenzyl)-3-(2-methylphenyl)-1,3,4-thiadiazol-2(3H)-one (compound 29). $^1$H-NMR (CDCl$_3$): 1.0 (t, 3H); 1.3 (d, 3H); 1.5-1.9 (m, 2H); 2.3 (s, 3H); 4.0 (s, 2H); 4.3 (m, 1H); 6.8-7.45 (complex, 8H).

3-(2-Chlorophenyl)-5-[4-(2-ethylhexyloxy)benzyl]-1,3,4-thiadiazol-2(3H)-one (compound 30). $^1$H-NMR (CDCl$_3$): 0.95 (m, 6H); 1.15-1.65 (complex, 8H); 1.75 (m, 1H); 3.85 (d, 2H); 4.0 (s, 2H); 6.8-7.6 (complex, 8H).

5-(4-Cyclopentoxybenzyl)-3-(2-chlorophenyl)-1,3,4-thiadiazol-2(3H)-one (compound 31). $^1$H-NMR (CDCl$_3$): 1.5-2.05 (complex, 8H); 4.0 (s, 2H); 4.75 (m, 1H); 6.8-7.6 (complex, 8H).

3-(2-Bromophenyl)-5-(4-sec-butoxybenzyl)-1,3,4-thiadiazol-2(3H)-one (compound 32). $^1$H-NMR (CDCl$_3$): 1.0 (t, 3H); 1.3 (d, 3H); 1.5-1.9 (m, 2H); 4.0 (s, 2H); 4.3 (m, 1H); 6.8-7.9 (complex, 8H).

3-(2-Chloro-4-fluorophenyl)-5-(4-iso-propoxybenzyl)-1,3,4-thiadiazol-2(3H)-one (compound 33). $^1$H-NMR (CDCl$_3$): 1.3 (d, 6H); 3.95 (s, 2H); 4.55 (m, 1H); 6.8-7.55 (complex, 7H).

5-[4-(3-Butin-2-oxy)benzyl]-3-(2-chlorophenyl)-1,3,4-thiadiazol-2(3H)-one (compound 34). $^1$H-NMR (CDCl$_3$): 1.65 (d, 3H); 2.5 (d, 1H); 4.0 (s, 2H); 4.85 (dq 1H); 6.9-7.6 (complex, 8H).

3-(2-Chlorophenyl)-5-[1-(4-iso-propoxyphenyl)ethyl]-1,3,4-thiadiazol-2(3H)-one (compound 35). $^1$H-NMR (CDCl$_3$): 1.35 (d, 6H); 1.65 (d, 3H); 4.15 (q, 1H); 4.55 (m, 1H); 6.85-7.6 (complex, 8H).

3-(2-Chlorophenyl)-5-[4-(2-ethylbutoxy)benzyl]-1,3,4-thiadiazol-2(3H)-one (compound 36). $^1$H-NMR (CDCl$_3$): 0.95 (t, 6H); 1.35-1.6 (m, 4H); 1.55-1.7 (m, 1H); 3.85 (d, 2H); 4.0 (s, 2H); 6.8-7.6 (complex, 8H).

EXAMPLE 13

2(2-Chlorophenyl)-5-(4-iso-propoxybenzyl)-4-methyl-2,4-dihydro-3H-1,2,4-triazol-3H-one (compound 13).

1.97 g (5.7 mmoles) of 3-(2-chlorophenyl)-5-(4-iso-propoxybenzyl)-1,3,4-oxadiazol-2(3H)-one (compound 2), 20 ml of dioxane and 20 ml of a 15% aqueous solution of methylamine are charged into a 100 ml 3-necked flask. The mixture is heated to reflux temperature for 3 hrs under stirring. It is left to cool to room temperature and 0.4 g (7.5 mmoles) of ground potassium carbonate are added; the mixture is brought again to reflux temperature for 8 h. The reaction mixture is then diluted with a saturated aqueous solution of ammonium chloride and extracted with ethyl acetate. The organic phase is washed with a saturated aqueous solution of sodium chloride, anhydrified with sodium sulphate and concentrated at reduced pressure. The reaction crude product is purified by silica gel chromatography using hexane/ethyl acetate 1:1 as eluant. 1.4 g of pure product are obtained.

$^1$H-NMR (CDCl$_3$): 1.25 (d, 6H); 3.0 (s, 3H); 3.75 (s, 2H); 4.4 (m, 1H); 6.6-7.5 (complex, 8H).

EXAMPLE 14

Determination of the miticide activity against the eggs of *Tetranychus urticae*.

Small disks taken from bean leaves were infested with mite eggs and then sprayed with a hydroacetonic solution of the product being tested.

The percentage of unopened eggs was determined after seven days of treatment compared with the percentage of eggs treated only with the hydroacetonic mixture. The results of evaluations carried out on dosages of 1 and 0.1 ppm are shown in the Table, which uses the following symbols:

5 = 91-100% of unopened eggs
4 = 80-90% of unopened eggs
3 = 60-79% of unopened eggs
2 = 40-59% of unopened eggs
1 = 20-39% of unopened eggs
0 = 0-19% of unopened eggs As a comparison, said Table shows the activity determined for 3-(2-chlorophenyl)-5-(2,6-dichlorophenyl)-1,3,4-oxadiazol-2(3H)-one (CR1), and for 3,5-bis-(2-chlorophenyl)-1,3,4-oxadiazol-2(3H)-one (CR2), described in European Patent Application 270061 (Examples 12 and 5, respectively, on page 38).

TABLE

| Compound | 1 ppm | 0.1 ppm |
|---|---|---|
| 2 | 5 | 1 |
| 4 | 5 | 5 |
| 5 | 5 | 5 |
| 12 | 5 | 4 |
| 14 | 5 | 3 |
| 16 | 5 | 5 |
| 17 | 5 | 4 |
| 19 | 5 | 5 |
| 20 | 5 | 5 |
| 22 | 5 | 4 |
| 25 | 5 | 5 |
| 26 | 5 | 5 |
| 27 | 5 | 4 |
| 28 | 5 | 2 |
| 29 | 5 | 5 |
| 30 | 5 | 5 |
| 31 | 5 | 5 |
| 32 | 5 | 5 |
| 34 | 5 | 5 |
| 35 | 5 | 5 |
| CR1 | 3 | 0 |
| CR2 | 4 | 0 |

We claim:
1. Oxadiazoles having the general formula:

$$\begin{array}{c} Y \\ \| \\ P-N-C-O \\ \phantom{P-N}\backslash\phantom{O}/ \\ \phantom{P-NN}N=C \\ \phantom{P-NN=C-}\backslash Q \end{array}$$

wherein:
Y represents O, S;
P represents an Fp group or a Bp group;
Q represents a Bq group when P=Fp, or an Fq group when P=Bp;

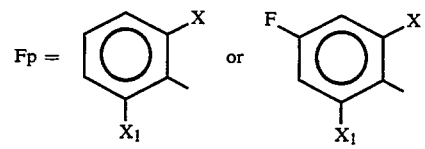

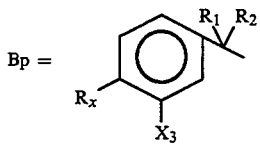

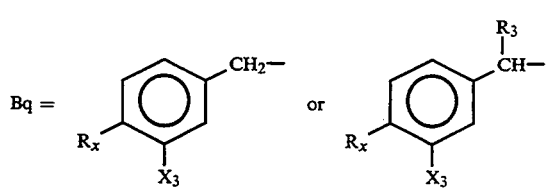

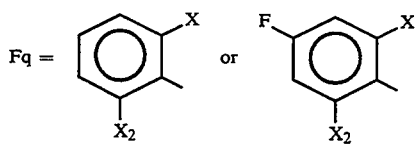

in said Fp, Fq, Bp and Bq groups:
X represents Cl, F, Br, Me, CF$_3$, MeO;
X$_1$ represents H or F;
X$_2$ represents H, F, or Cl;
X$_3$ represents H, F, Cl or a C$_1$–C$_4$ alkoxy;
R$_1$ and R$_2$ independently represent H or a C$_1$–C$_3$ alkyl
R$_x$ represents a C$_3$–C$_{10}$ alkoxy, a C$_3$–C$_8$ alkenyloxy, a C$_3$–C$_8$ alkinyloxy, a C$_3$–C$_8$ cycloalkoxy, a C$_4$–C$_8$ cycloalkylalkoxy, a C$_3$–C$_{10}$ alkoxyalkoxy all optionally halogenated, or a phenoxy or a phenylalkoxy optionally substituted by halogen atoms, alkyl groups, haloalkyl groups, alkoxy groups, haloalkoxy groups; and
R$_3$ represents a C$_1$–C$_3$ alkyl.

2. Oxadiazoles having the general formula:

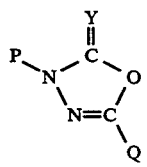

wherein:
Y represents O, S
P represents an Fp group or a Bp group;
Q represents a Bq group when P=Fp, or an Fq group when P=Bp;

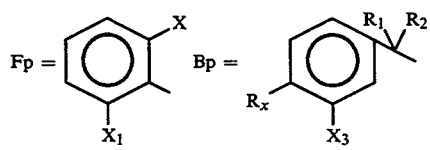

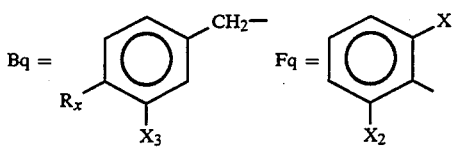

in said Fp, Fq, Bp and Bq groups:
X represents Cl, F, Br, Me, CF$_3$, MeO;
X$_1$ represents H or F;
X$_2$ represents H, F, or Cl;
X$_3$ represents H, F, Cl or a C$_1$–C$_4$ alkoxy;
R$_1$ and R$_2$ independently represent H or a C$_1$–C$_3$ alkyl;
R$_x$ represents a C$_1$–C$_{10}$ alkyl, a C$_3$–C$_8$ cycloalkyl, a C$_4$–C$_8$ cycloalkylalkyl, a C$_3$–C$_{10}$ alkoxy, a C$_3$–C$_8$ cycloalkoxy, a C$_4$–C$_8$ cycloalkylalkoxy, a C$_3$C$_{10}$ alkoxyalkoxy all optionally halogenated, or a phenoxy or a phenylalkoxy optionally substituted by halogen atoms, alkyl groups, haloalkyl groups, alkoxy groups, haloalkoxy groups.

3. Oxadiazol- ones(thiones) having the general formula:

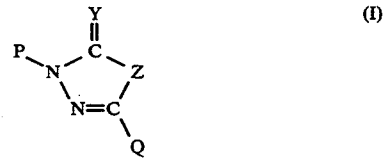

wherein:
Y represents O, S;

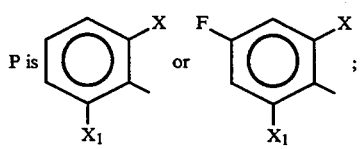

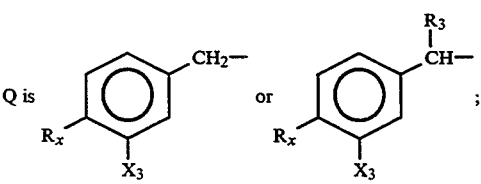

X represents Cl, F, Br, Me, CF$_3$, MeO;
X$_1$ represents H or F;
X$_3$ represents H, F, Cl or a C$_1$–C$_4$ alkoxy;
R$_x$ represents a C$_3$–C$_{10}$ alkoxy, a C$_3$–C$_8$ alkenyloxy, a C$_3$–C$_8$ alkinyloxy, a C$_3$–C$_8$ cycloalkoxy, a C$_4$–C$_8$ cycloalkylalkoxy, a C$_3$–C$_{10}$ alkoxyalkoxy all optionally halogenated, or a phenoxy or a phenylalkoxy optionally substituted by halogen, alkyl, haloalkyl, alkoxy or haloalkoxy; and
R$_3$ represents a C$_1$–C$_3$ alkyl.

4. Oxadiazol- ones(thiones) having the general formula:

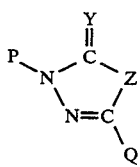

(I)

wherein:
Y represents O, S
Z represents O

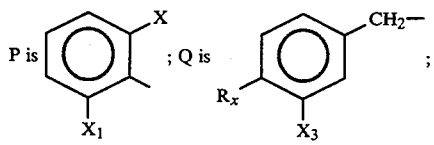

X represents Cl, F, Br, Me, CF$_3$ or MeO;
X$_1$ represents H or F;
X$_3$ represents H, F, Cl or a C$_1$–C$_4$ alkoxy; and
R$_x$ represents a C$_1$–C$_{10}$ alkyl, a C$_3$–C$_8$ cycloalkyl, a C$_4$–C$_8$ cycloalkylalkyl, a C$_3$–C$_{10}$ alkoxy, a C$_3$–C$_8$ cycloalkoxy; a C$_4$–C$_8$ cycloalkylalkoxy, a C$_3$–C$_{10}$ alkoxyalkoxy all optionally halogenated, or a phenoxy or a phenylalkoxy optionally substituted by halogen, alkyl, haloalkyl, alkoxy or haloalkoxy.

5. The compound according to claim 1 as 5-(4-sec-Butoxybenzyl)-3-(2-chloro-phenyl)-1,3,4-oxadiazol-2(3H)-one (compound 4).

6. The compound according to claim 1 as 5-(4-Cyclopentoxybenzyl)-3-(2-chlorophenyl)-1,3,4-oxadiazol-2(3H)-one (compound 16).

7. The compound according to claim 1 as 5-[4-(3-Butin-2-oxy)benzyl]-3-(2-chlorophenyl)-1,3,4-oxadiazol-2(3H)-one (compound 19).

8. The compound according to claim 1 as 3-(2-Chlorophenyl)-5-[1-(4-iso-propoxyphenyl)ethyl]-1,3,4-oxadiazol-2(3H)-one (compound 20).

9. Miticide and insecticide compositions containing an effective quantity of one or more of the compounds according to claim 1, together with solid or liquid carriers, and optionally other additives.

10. Method for fighting harmful insect and mite infestations consisting of distributing an effective quantity of one or more of the compounds according to claim 1, over the infested area.

* * * * *